United States Patent [19]

Ungar et al.

[11] Patent Number: 4,649,936

[45] Date of Patent: * Mar. 17, 1987

[54] ASYMMETRIC SINGLE ELECTRODE CUFF FOR GENERATION OF UNIDIRECTIONALLY PROPAGATING ACTION POTENTIALS FOR COLLISION BLOCKING

[75] Inventors: Ira J. Ungar, Shaker Heights; J. Thomas Mortimer, Cleveland Heights, both of Ohio

[73] Assignee: Case Western Reserve University, Cleveland, Ohio

[ * ] Notice: The portion of the term of this patent subsequent to Dec. 16, 2003 has been disclaimed.

[21] Appl. No.: 659,781

[22] Filed: Oct. 11, 1984

[51] Int. Cl.$^4$ ............................................. A61N 1/04
[52] U.S. Cl. ................................. 128/784; 128/421
[58] Field of Search ............................... 128/784–785, 128/642, 419 C, 419 R, 802, 421

[56] References Cited

U.S. PATENT DOCUMENTS

| | | | |
|---|---|---|---|
| Re. 26,810 | 3/1970 | Schwartz et al. | 128/784 |
| 3,157,181 | 11/1964 | McCarty | 128/784 |
| 3,654,933 | 4/1972 | Hagfors | 128/784 |
| 3,738,368 | 6/1973 | Avery et al. | 128/784 |
| 3,774,618 | 11/1973 | Avery | 128/784 |
| 4,341,221 | 7/1982 | Testerman | 128/642 |

OTHER PUBLICATIONS

"A Technique for Collision Block of Peripheral Nerve: Single Stimulus Analysis", IEEE Trans. on Biomed. Eng., vol. BME-28, No. 5, May 1981.

"A Technique for Collision Block of Peripheral Nerve: Frequency Dependence", IEEE Trans. on Biomed. Engr., vol. BME-28, No. 5, May 1981.

"Generation of Unidirectionally Propagated Action Potentials in a Peripheral Nerve by Brief Stimuli", Science, vol. 206, pp. 1311–1312, Dec. 1979.

*Primary Examiner*—William E. Kamm
*Attorney, Agent, or Firm*—Fay, Sharpe, Fagan, Minnich & McKee

[57] ABSTRACT

A single electrode, asymmetric electrode cuff (B) is disposed around a nerve trunk (A). A signal generator (C) is connected between a cathode (20) disposed asymmetrically in the electrode cuff and an anode (22) disposed in an electrically conductive relationship within the body tissue. The signal generator applies a stimulus signal (FIG. 3) which generates unidirectionally propagating action potentials on the nerve trunk. The electrode cuff includes a dielectric sleeve (10) in which the cathode is positioned a first distance (L1) from an escape end (14) and a second distance (L2) from an arrest end (16). The first distance is at least 1.7, and preferably about 7, times the second distance. This asymmetry causes a primary or forward stimulus signal current (30) to be correspondingly greater than a secondary or reverse current (32).

13 Claims, 3 Drawing Figures

ASYMMETRIC SINGLE ELECTRODE CUFF FOR GENERATION OF UNIDIRECTIONALLY PROPAGATING ACTION POTENTIALS FOR COLLISION BLOCKING

BACKGROUND OF THE INVENTION

The present invention relates to the biomedical arts for introducing electrical signals on nerve trunks. The present invention finds particular application in inducing a stream of artifically generated antidromic pulses on the nerve trunk for collision blocking orthodromic pulses moving in the opposite direction on the nerve trunk and will be described with particular reference thereto. It is to be appreciated, however, that the invention may have broader applications including generating action potentials on nerve trunks for other purposes and monitoring naturally occuring nerve impulses.

Heretofore, various techniques have been used to block nerve pulses passing along a nerve trunk. Commonly, an electrode cuff including a dielectric sleeve and three symmetric electrodes were positioned around a nerve trunk. The three electrodes were arranged symmetrically within the sleeve, with an annular cathode positioned in the center and a pair of annular anodes were positioned to either side. A signal generator was connected with the electrodes to apply an electrical pulse train that induced action potentials on the nerve trunk.

One blocking technique was the application of DC currents on the nerve trunk. However, it has been found that the application of DC and unidirectionally pulsed currents induced nerve damage.

To eliminate the DC current induced nerve damage, others have used a bipolar current wave forms such that the average electrical charge passed through an electrode is approximately zero. In one technique, a train of pulses was applied to the cuff electrodes. Each pulse of an exemplary pulse train included a rapid rise to a preselected amplitude, a 200 to 1000 microsecond plateau, and an exponential decay back to zero. The ends of the cuff have been defined as the "arrest" end and the "escape" end. No action potential was intended to emerge from the "arrest" end and the colliding pulse emerges from the "escape" end. This pulse train induced artifically generated antidromic pulses traveling unidirectionally on the nerve trunk. The antidromic pulses collided with and blocked orthodromic pulses traveling in the other direction. To eliminate nerve damage that may result from monopolar stimulation, a relatively long duration, low amplitude rectangular pulse of opposite polarity was applied between each pulse of the first polarity pulse train.

Although it was intended that current should flow within the cuff from the anodes to the cathode, some current (secondary current) also flowed outside the cuff in the body tissue, creating a virtual cathode along the nerve outside the cuff. This secondary current tended to generate unwanted action potentials near the arrest end of the cuff that traveled along the nerve trunk in the orthodromic or undesired direction.

The present invention contemplates a new and improved apparatus and method for generating action potentials which eliminates virtual cathodes.

SUMMARY OF THE INVENTION

In accordance with the present invention, there is provided an asymmetric, single electrode cuff. The cuff includes a sleeve of non-conducting, bicompatible material. The sleeve defines an axial passage therethrough extending from an arrest end to an escape end. The passage is adapted to receive a nerve trunk therethrough with the escape end disposed toward the origin of orthodromic pulses. An annular electrode is disposed in the axial sleeve passage, offset closer to the arrest end than the escape end.

In accordance with a more limited aspect of the present invention, an apparatus is provided for blocking orthodromic pulses passing along a nerve. The apparatus includes an asymmetric, single electrode cuff substantially as described in accordance with the first aspect of the invention. A signal generator biases the single electrode to function as a cathode and biases an electrode operatively disposed in body tissue, at a site removed from the cuff, as an anode. The signal generator generates a train of pulses which artificially generate a stream of antidromic pulses which travel unidirectionally from the cuff along the nerve trunk and collision block any orthodromic pulses.

One advantage of the present invention is that orthodromic pulses are blocked safely and efficiently.

Another advantage of the present invention is that the tendency to generate unwanted action potentials at sites outside the cuff (i.e., virtual cathodes) is reduced or eliminated.

A further advantage resides in a lowering of the electrical power and/or charge required for reliably generating action potentials.

Yet other advantages of the present invention will become apparent to those of ordinary skill in the art upon reading and understanding the following detailed description of the preferred embodiments.

BRIEF DESCRIPTION OF THE DRAWINGS

The invention may take form in various parts and arrangements of parts or in various steps and combinations of steps. The drawings are only for purposes of illustrating a preferred embodiment of the invention and it should not be construed as limiting it.

DETAILED DESCRIPTION OF THE PREFERRED EMBODIMENTS

Figure 1:
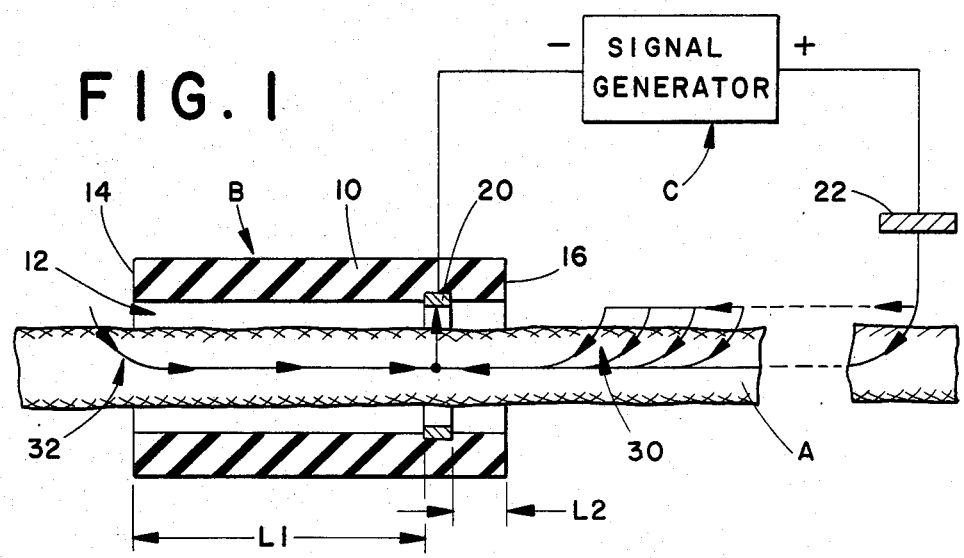
FIG. 1 is a diagrammatic illustration of an action potential generating system, in partial section, in accordance with the present invention.

With particular reference to FIG. 1, a nerve trunk A extends through a central passage of an electrode cuff B. A signal generating means C applies the appropriate electrical potentials to body tissue, at least in part through the electrode cuff, for introducing a string of artifically generated antidromic pulses or other action potentials along the nerve trunk A.

The nerve trunk A includes a plurality of nerve fibers including an axis of axoplasm surrounded by regularly spaced myelin sheaths. The axon of each nerve cell under certain physiological conditions conducts electrical pulses from the dendrites and cell body to the axon, i.e., orthodromic conduction. In response to an appropriate electric current, electrical action potentials traveling opposite the orthodromic pulses can be induced, i.e., antidromic pulses.

Figure 2:
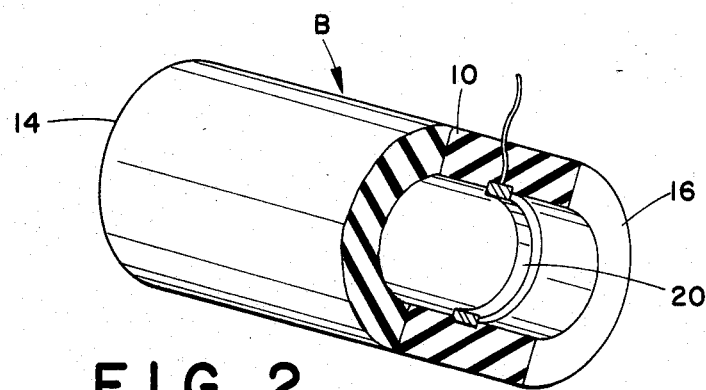
FIG. 2 is a perspective view of an asymmetric, single electrode cuff, in partial section in accordance with the present invention; and, FIG. 3 is an antidromic pulse generating wave form in accordance with the present invention.

With reference to FIGS. 1 and 2, the electrode cuff B includes an electrically non-conductive or dielectric sleeve 10 which defines an axial current passage 12 therethrough. The dielectric sheath and axial passage extend from a first or escape end 14 disposed toward the origin of the orthodromic pulses to a second or arrest end 16. To receive the nerve trunk non-compressively, the central passage is larger (e.g. 30%) in diameter than the nerve trunk. The gap between the nerve trunk and the cuff is filled by conductive body tissues and fluids after implantation in the body. The axial passage 12 and the dielectric sheath are both circular in transverse cross section for simplicity of construction. However, it is contemplated that certain elliptical and other non-circular cross sections may also be suitable.

A single, annular electrode 20 is disposed in the axial passage. The electrode may be mounted on the inner surface of the dielectric sleeve within the axial passage provided that the electrode allows the nerve trunk A to pass uncompressed therethrough. Alternately, the electrode may be recessed into the dielectric sleeve such that its inner surface is flush with or below the level of the dielectric passage. The electrode is positioned a length L1 from the escape end 14 and a length L2 from the arrest end 16. The electrode is disposed asymmetrically within the dielectric sleeve toward the arrest end, i.e., length L1 is greater than length L2. More particularly, it has been found that excellent results are achieved when the length L1 is between 1.7 and 7 times the length L2. Ratios greater than 7:1 also generate satisfactory antidromic pulses, but the resulting electrode cuff may be so long that its length tends to interfere with convenient implantation. Satisfactory results are achieved for a 1 mm nerve trunk with the length L1 equal to 21 mm and the length L2 equal to 3 mm.

with continuing reference to FIG. 1, the signal generator C generates a pulse train which it applies between the cuff electrode 20 and a second electrode 22. The second electrode is disposed separately in the patient's body in an electrically conductive relationship to the nerve trunk A. Preferably, the second electrode is biased to function as an anode and is disposed to a site remote from the electrode cuff B to facilitate a primary or forward current flow 30 from the anode 22, through the nerve trunk, to the cuff electrode 20.

Because the body fluids and tissues are electrically conductive, a secondary or reverse current 32 from the anode 22 also flows into the nerve trunk A upstream from the escape end 14 of the electrode cuff. If the reverse current 32 has a sufficiently high amplitude, it can cause arrest of the antidromic action potential at the escape end 14. The relative amplitude of the forward and reverse currents varies in proportion to the asymmetry of the cuff electrode within the dielectric sleeve 10. That is, the more asymmetrically the cuff electrode 20 is positioned, i.e., the greater the ratio of the first length L1 to the second length L2, the greater the relative difference between the forward and reverse currents. By placing the cuff electrode sufficiently asymmetrically, a unidirectional flow of antidromic pulses along the nerve trunk is generated flowing from the cuff arrest end.

More specifically, the generation of unidirectional action potentials is commonly preceded by bidirectional propagation as the amplitude of the stimulus signal from the signal generator increases from zero. If the stimulus signal amplitude increases beyond an appropriate unidirectional blocking amplitude, the reverse current 32 also reaches the blocking amplitude and blocking of antidromic pulses occurs. Between the initial bidirectional action potential escape and the bidirectional blocking of action potentials, a unidirectional block window is defined. Because the relative amplitudes of the forward current 30 and the reverse current 32 vary with the asymmetry of the cathode electrode 20 within the cuff, the width of the unidirectional block window also varies with the electrode asymmetry. Further, the block window width varies with other factors which affect relative current flow such as the diameter of the axial passage 12, the length of the electrode cuff, and the like.

Figure 3:
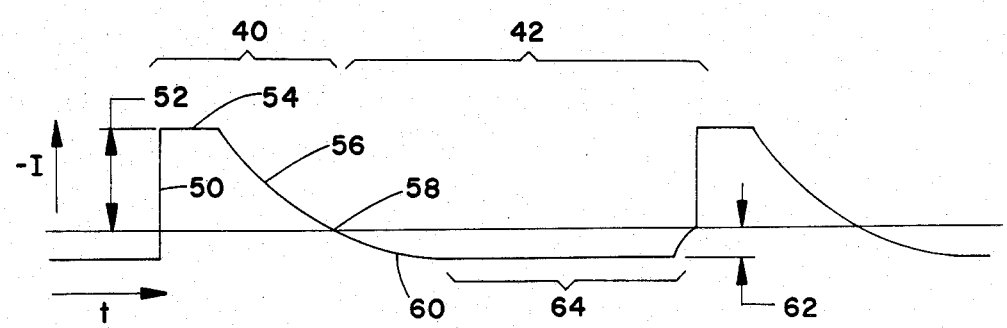

With particular reference to FIG. 3, the signal generator C generates a series of regularly spaced, substantially identical pulses. The stimulation signal may have a frequency of about 1 hertz up to 100 hertz or more. Each pulse cycle includes a first portion 40 having a first polarity and a second portion 42 having a second or opposite polarity. The second portion 42 may not be required in all applications. The first polarity portion 40 includes a leading edge 50 which rises rapidly to a preselected amplitude 52. Amplitudes of $\frac{1}{4}$ to 20 milliamps have been found to be satisfactory. As a specific example, for a 1 mm nerve trunk A, a 24 mm electrode cuff with a 1.65 mm axial passage diameter, and an asymmetry of 7:1 achieved unidirectional action potential generation in window between about $\frac{1}{4}$ and $1\frac{3}{4}$ milliamps. Each first polarity pulse further has a plateau portion 54 which maintains the amplitude for a preselected duration. The plateau portion 54 lasts for 100 to 3000 microseconds. After the preselected duration, the amplitude decays exponentially along an exponential decay portion 56 reaching zero amplitude at a crossover point 58.

In the second portion 42, if it is used, the current changes polarity and increases in amplitude along an exponential current increase portion 60. At the interface or crossover point 58, the one polarity decay portion 56 and the opposite polarity increase portion 60 have a smooth, discontinuity-free transition. Although the one polarity decay and the other polarity increase portions follow a common curve in the preferred embodiment, they may follow different smooth curves provided there is substantially no discontinuity at the interface. The opposite polarity increase portion reaches a steady state amplitude 62 and holds the steady state amplitude for a steady state duration 64 until the next cycle begins with a substantially identical pulse. The opposite polarity current amplitude 62 is sufficiently small that the reverse polarity current induces no action potentials on the wave trunk. The decay constant of the exponential decay portion 56 and the opposite polarity amplitude 62 are selected such that the total charge flow in the first 40 and second 42 portions of each cycle are equal and opposite. In this manner, there is no net charge transfer. It is to be appreciated that opposite polarity pulses or portions of various shapes may be utilized provided the amplitude remains low and there are substantially no discontinuities.

With particular reference to FIG. 1 in operation, the electrode cuff B is surgically implanted around the nerve to be controlled. The signal generator is connected with the electrode cuff electrode 20 and the anode electrode 22. During the first polarity pulse portion of each cycle, the forward current 30 flows from the anode, through the tissue, and along the nerve trunk. The forward current increases adjacent the cuff, reaching a maximum current density adjacent the cathode 20. More specifically, current flows from the anode through body tissues and enters the axoplasm of the nerve between myelin sheath segments. The entering current hyperpolarizes the nerve at Ranvier nodes near the ends of the electrode cuff. The current exits, or depolarizes, the nerve at a node closely adjacent the cathode. The current reaches a sufficient current density adjacent the cathode 20 that a propagating action potential is created at this site. The action potential is propagated in both the antidromic and orthodromic directions. Each antidromic action potential travels along the nerve trunk toward the escape end of the cuff and therebeyond to collide with and annihilate a naturally generated orthodromic pulse moving toward the cuff. The orthodromically propagating action potential is arrested at the arrest end 16 by maintaining the hyperpolarizing current 30 for the period of time required to oppose the depolarizing currents of the approaching electrically generated orthodromic action potential. Typically this time is 500 microseconds, but may vary from 100 microseconds to 3000 microseconds.

Positioning the cathode closer to one end of the cuff, i.e., more asymmetrically, selects the fraction of stimulus current which enters the nodes at each cuff end. The cuff end closer to the cathode receives the larger share of the current and is commonly referred to as the arrest end of the cuff.

The current flow decays or decreases smoothly such that no additional pulses are generated. After the zero crossing point 58, the second or opposite polarity pulse portion causes a small but longer duration charge flow in the opposite direction. The opposite polarity pulse portion is of the appropriate amplitude and duration to cause the same net amount of charge transfer as the higher amplitude but shorter first polarity pulse portion. Although the opposite polarity pulse portion does not excite the nerve trunk, it balances the net charge transfer therealong.

The invention has been described with reference to the prefered embodiments. Obviously, modifications and alterations will occur to others upon reading and understanding the preceding detailed description of the preferred embodiments. It is intended that the invention be construed as including all such alterations and modifications insofar as they come within the scope of the appended claims or the equivalents thereof.

Having thus described a preferred embodiment of the invention, the invention is now claimed to be:

1. An asymmetric single electrode cuff system comprising:
   a sleeve of electrically non-conductive, biocompatible material, the sleeve defining an axial passage therethrough from a first end to a second end, which passage is adapted to receive a nerve trunk therethrough,
   one and only one annular electrode extending radially around an inner surface of the axial sleeve passage, the electrode being disposed closer to the first end than the second end,
   a remote electrode physically disconnected and displaced from the axial sleeve, and,
   a signal generator electrically connected with the axial sleeve electrode and the remote electrode for applying an oscillating current thereacross.

2. The electrode cuff system as set forth in claim 1 wherein the annular electrode defines a circular passage therethrough.

3. An asymmetric single electrode cuff comprising:
   a sleeve of electrically non-conductive, biocompatible material, the sleeve defines an axial passage therethrough from a first end to a second end, which passage is adapted to receive a nerve trunk therethrough, and,
   one and only one annular electrode is disposed in the axial sleeve passage, the electrode is disposed a first distance from the first end and a second distance from the second end, the first distance is at least 1.7 times as large as the second distance.

4. The electrode cuff as set forth in claim 3 wherein the first distance is 7 times the second distance.

5. The electrode cuff as set forth in claim 4 wherein the first distance is 21 mm, the second distance is 3 mm, and the electrode has an inner diameter of about 1 mm to 2 mm.

6. An action potential blocking system for selectively, unidirectionally blocking orthodromic action potentials passing along a nerve trunk, the system comprising:
   an electrode cuff including only a single electrode encircled by a dielectric sleeve, the dielectric sleeve extending a first distance from one side of the single electrode to an escape end and extending a second distance from the other side of the single electrode to an arrest end, the first distance being greater than the second distance, the single electrode and dielectric sleeve being disposed around the nerve trunk;
   a remote electrode disposed physically displaced and separated from the electrode cuff;
   a signal generator electrically connected with the electrodes for applying a stimulus current across the electrodes to generate antidromic action potentials in the nerve trunk to collision block the orthodromic action potentials.

7. The blocking system as set forth in claim 6 wherein the signal generator includes an oscillator for generating the stimulus current such that the stimulus current oscillates cylically, each oscillation cycle of the stimulus current having a first polarity portion and an opposite polarity portion.

8. The blocking system as set forth in claim 6 wherein the first distance is at least 1.7 times the second distance.

9. The blocking system as set forth in claim 8 wherein the first distance is about 7 times the second distance.

10. A method of blocking orthodromic action potentials traveling along a nerve trunk in a first direction, the method comprising:
    positioning an electrode cuff, which has a dielectric sleeve extending from an escape end to an arrest end and only a single electrode disposed in the dielectric sleeve closer to the arrest end than the escape end, around the nerve trunk such that the orthodromic action potentials travel from the escape end toward the arrest end;
    positioning a remote electrode physically separate from the cuff in an electrically conductive relationship with the nerve trunk;
    applying an oscillating, bipolar stimulating electric signal across the electrodes, the bipolar signal including a first polarity portion of each cycle for generating antidromic action potentials traveling unidirectionally along the nerve trunk in an opposite direction to the orthodromic action potentials, the antidromic action potentials collision blocking the orthodromic action potentials from traveling past the electrode cuff.

11. An action potential blocking system for selectively, unidirectionally blocking orthodromic action potentials passing along a nerve trunk, the system comprising:
an electrode cuff including one and only one electrode encircled by a dielectric sleeve, the dielectric sleeve extending a first distance from one side of the single electrode to an escape end and extending a second distance from the other side of the single electrode to an arrest end, the single electrode and dielectric sleeve being disposed around the nerve trunk;
a remote electrode displaced separate from the electrode cuff;
an oscillating means for generating a cylically oscillating current which has oscillation cycles that each include a first polarity portion and a second polarity portion, the first and second polarity portions of each cycle having a balanced net change flow; and,
a means for applying the oscilalting current across the cuff electrode and the remote electrode such that the first polarity portions generate unidirectional antidromic action potentials traveling along the nerve trunk from the electrode cuff escape end and the second polarity portions balance net charge flow in the nerve trunk without generating an action potential.

12. The blocking system as set forth in claim 11 wherein the first distance is at least 1.7 times the second distance.

13. The blocking system as set forth in claim 12 wherein the first distance is about 7 times the second distance.

* * * * *